United States Patent [19]

Asami et al.

[11] Patent Number: 5,460,802
[45] Date of Patent: Oct. 24, 1995

[54] ORAL DISINFECTANT FOR COMPANION ANIMALS

[75] Inventors: Takao Asami, Mitaha; Manabu Takhashi, Matsudo, both of Japan; Jeffrey F. Andrews, Stillwater; Thomas E. Boettcher, Hastings, both of Minn.

[73] Assignee: Minnesota Mining and Manufacturing Company, St. Paul, Minn.

[21] Appl. No.: 276,531

[22] Filed: Jul. 18, 1994

[51] Int. Cl.⁶ ................ A61K 7/16; A61K 7/24
[52] U.S. Cl. ............ 424/49; 424/55; 514/835; 514/901; 514/902; 514/784; 514/785
[58] Field of Search .............. 424/4, 9, 50, 55; 514/785, 835, 901, 902, 784

[56] References Cited

U.S. PATENT DOCUMENTS

| | | | |
|---|---|---|---|
| 4,002,775 | 1/1977 | Kabara | 426/532 |
| 4,067,997 | 1/1978 | Kabara | 424/312 |
| 4,160,820 | 7/1979 | Wagenknecht et al. | 424/48 |
| 4,189,481 | 2/1980 | Kabara | 424/248.54 |
| 4,363,763 | 12/1982 | Peterson | 260/410.7 |
| 4,469,635 | 9/1984 | Peterson | 260/403 |
| 4,722,941 | 2/1988 | Eckert et al. | 514/784 |
| 4,921,694 | 5/1990 | Hoppe et al. | 424/65 |
| 4,952,407 | 8/1990 | Record et al. | 424/440 |
| 5,130,056 | 7/1992 | Jakobson et al. | 252/551 |
| 5,182,100 | 1/1993 | Klueppel et al. | 424/49 |
| 5,208,257 | 5/1993 | Kabara | 514/552 |
| 5,219,887 | 6/1993 | Andrews et al. | 514/552 |
| 5,378,731 | 1/1995 | Andrews et al. | 514/552 |

FOREIGN PATENT DOCUMENTS

| | | | |
|---|---|---|---|
| 0243145B1 | 4/1987 | European Pat. Off. | A61K 31/20 |
| 0244144 | 4/1987 | European Pat. Off. | A23L 3/34 |
| 0367939B1 | 9/1989 | European Pat. Off. | A61K 7/08 |
| 2755052 | 6/1978 | Germany | A61L 13/00 |
| WO92/21320 | 12/1992 | WIPO | A61K 7/06 |

OTHER PUBLICATIONS

Nakagaki et al., "Solubility and Hydrolysis Rate of 1–Monolaurin in Aqueous Solutions", Yakugaku Zasshi, vol. 90 (10) 1310–1315 (1970).

Kato et al., Abstract, "Combined Effect of Different Drugs on the Antibacterial Activity of Fatty Acids and Their Esters", vol. 3, No. 8 (1975).

Kato et al., Abstract, "Combined Effect of Critic and Polyphosphoric Acid on the Antibacterial Activity of Monoglycerides", vol. 4, No. 6 (1976).

Kabara, "GRAS Antimicrobial Agents for Cosmetic Products", *J. Soc. Cosmet. Chem.*, 31, 1–10 (Jan./Feb. 1980).

Abstract, CH 634 749, Feb. 28, 1983.

Kabara, "Medium–Chain Fatty Acids and Esters as Antimicrobial Agents", *Cosmetic and Drug Preservation*, (16), 1984, pp. 275–304.

Schemmel et al., "Monolaurin As An Anticaries Agent", Chapter 4, Symposium on the Pharmacological Effect of Lipids, pp. 37–43 (1983).

*Primary Examiner*—Arthur C. Prescott
*Attorney, Agent, or Firm*—Gary L. Griswold; Walter N. Kirn; Paul W. Busse

[57] ABSTRACT

The present invention is generally related to an oral disinfectant for companion animals. A preferred disinfectant is a concentrated composition containing a fatty acid monoester, one or more fatty acids, an acid or chelating agent, a polyalcohol, a surfactant and water. When used the concentrate is diluted with water and then applied to the teeth and oral cavity tissues of the animal.

10 Claims, 2 Drawing Sheets

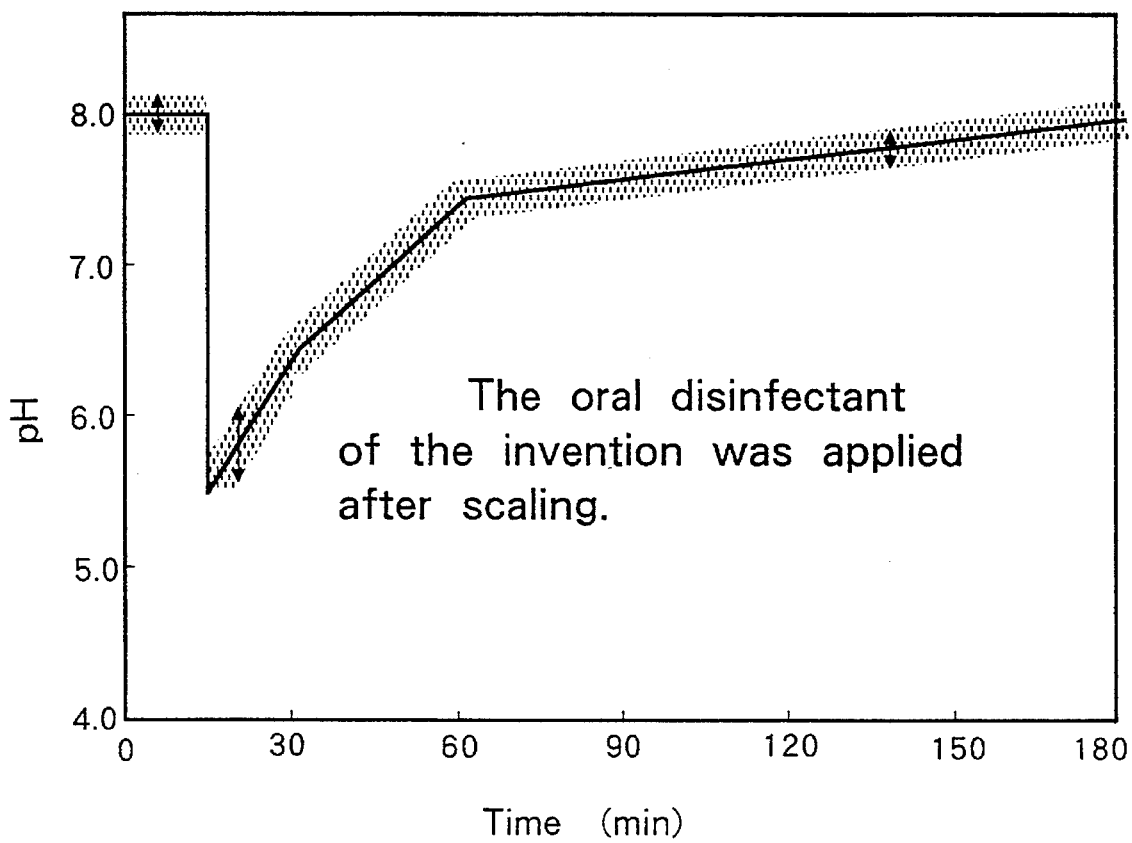

ORAL DISINFECTANT FOR COMPANION ANIMALS

The present invention relates to an oral disinfectant for companion animals such as domestic dogs and cats.

BACKGROUND

The oral cavity of companion animals is composed of both hard tissue such as teeth and soft tissues such as a tongue, gingivae, periodontia, etc. The oral cavity participates in several physical activities, e.g., chewing foods, as well as in chemical activity, i.e., saliva production. Accordingly, the health care for the oral cavity is different from that for the other organs, and sanitary care of the oral cavity is important. For example, dogs and cats are popular companion animals and oral hygiene for them is different from that for human beings since general brushing of teeth of such animals may be very difficult. Therefore, the oral cavity of such animals may often be extremely unsanitary.

In addition, the hydrogen ion concentration or pH value in the oral cavity of dogs and cats is 8.0 or higher so that bacteria such as *Escherichia coli* and other various putrefying microbes grow in the cavity and make it unsanitary. Putrefying microbes include anaerobic microbes such as Bacteroides, anaerobic Streptococcus, Clostridium, Vaillonella, etc., as well as aerobic bacteria such as *Escherichia coli, Pseudomonas aeruginosa,* Proteus, and Staphylococcus. Furthermore, food residues adhered to teeth may form plaque containing salivary bacteria. About 70 to 80% of plaque is water, while the remaining content includes proteins. Such proteins are decomposed by putrefying microbes to form offensive substances such as ammonia, hydrogen sulfide, amines, indoles, phenols, mercaptans, etc. The number of salivary bacteria is from $10^7$ to $10^{11}$ bacteria per ml of saliva, and includes not only gram-positive bacteria but also various gram-negative bacteria which grow and proliferate in saliva. Microbes in plaque typically include Bacteroides, Gingivalis, Actinobacillus and Actinomycetamcomitans. These gram-negative microbes produce endotoxins that may cause systemic disorders in animals. In addition, they may cause local oral disorders such as halitosis, gingivitis, periodontitis, and often stomatitis, etc., which may be accompanied by pain and pus or loose teeth.

When inorganic salts such as calcium phosphate contained in saliva deposit on plaque, a calcified substance, tartar, is formed. Tartar frequently presses against gingivae and periodontal membranes and causes inflammations of these tissues. Tartar also induces further deposition and accumulation of plaque on teeth, and the resulting toxins and acids from parasitized bacteria may damage or destroy periodontia.

To control periodontitis and plaque in humans both mechanical means such as brushing, scaling and root planing and chemical means such as mouth washing are used. However, since brushing cannot be easily applied in daily home care for companion animals, especially dogs and cats, a chemical means is a preferred method to ensure a hygienic condition in their oral cavity.

The following chemical methods have been used as chemical plaque-controlling agents for companion animals. See for example, "Why carious teeth are formed", Iwanami Shin-sho by S. Hamada, pp. 131–133.

Chlorhexidine Gluconate Solution

An aqueous chlorhexidine gluconate solution has a pH value of from 5.5 to 7.3 and is effective against both gram-positive and gram-negative microbes. However, application of this solution to mucous membranes is not desired because it will yellow the oral cavity and some microbes become resistant to it when used for a long time. In addition, it does not significantly lower the pH value in the oral cavity.

Chlorhexidine Hydrochloride Solution

An aqueous chlorhexidine hydrochloride solution has a pH value of from 5.5 to 7.0 and is also effective against both gram-positive and gram-negative microbes. However, the effects of this solution appear slowly and it does not significantly lower the pH value in the oral cavity.

Iodine Solution

An iodine solution has a pH value of from 5.5 to 6.0 and has anti-microbial activity against gram-positive and gram-negative microbes. However, this solution is not desired because it yellows the area to which it has been applied and, if used for a long period of time, may cause thyroid disorders.

Antibiotics

Antibiotics may be used for both systemic and/or local application to the oral cavity and may exterminate pathogenic bacteria when used to treat periodontitis disorders. However, antibiotics do not remove bacteria or endotoxins that may be firmly adhered to the surfaces of teeth. For local application, use of minocycline hydrochloride is known. However, when antibotics such as minocycline hydrochloride are used for a long period of time, antibiotic resistant microbes may result.

Oral disorders in companion animals such as dogs and cats, such as stomatitis as well as periodontal diseases, gingivitis, marginal periodontitis, and apical periodontitis, typically develop because plaque (a primary cause of such oral disorders) cannot be controlled by daily mechanical means such as brushing of teeth. The present invention provides a composition which disinfects the oral cavity and may be used to prevent or treat oral disorders such as stomatitis, periodontal diseases, gingivitis, marginal periodontitis, apical periodontitis, etc. by chemical means.

SUMMARY OF THE INVENTION

In view of the observation that the oral cavities of companion animals such as dogs and cats generally have high pH values the present invention was developed, in part, to lower pH values of an animal's oral cavity with the use of safe, acidic substances which exterminate various bacteria and prevent bacterial propagation.

This invention provides an oral disinfectant for companion animals wherein the animal's teeth and oral cavity tissues are treated with a composition comprising (a) 0.1–3 wt % of a fatty acid monoester selected from the group consisting of glycerol and propylene glycol monoesters of a $C_6$–$C_{14}$ fatty acid;

(b) about 0.5–10 wt % of a $C_6$–$C_{14}$ fatty acid;

(c) about 2–10 wt % of an acid or chelating agent selected from the group consisting of lactic acid, tartaric acid, adipic acid, succinic acid, citric acid, ascorbic acid, malic acid, mandelic acid, acetic acid, sorbic acid, sodium acid pyrophosphate, acidic sodium hexametaphosphate, ethylenediaminetetraacetic acid and salts thereof, and mixtures thereof;

(d) about 10–50 wt % of a polyalcohol;

(e) about 2–30 wt % of a surfactant; and (g) water for the balance.

A preferred oral disinfectant composition for companion animals comprises (a) about 0.1–3 wt % glycerol monoester of lauric acid;

(b) about 0.5–10 wt % caprylic acid or capric acid or a mixture thereof;

(c) about 2–10 wt % lactic acid or citric acid or a mixture thereof;

(d) about 10–50 wt % propylene glycol;

(e) about 5–15 wt % polyoxyethylene-polyoxypropylene block copolymer; and (f) water for the balance.

A highly preferred oral disinfectant composition for companion animals comprises (a) about 0.5–1.5 wt % glycerol monoester of lauric acid;

(b) about 1.8–3.8 wt % caprylic acid;

(c) about 1–3 wt % capric acid;

(d) about 4–8 wt % lactic acid;

(e) about 15–30 wt % propylene glycol;

(f) about 5–15 wt % polyoxyethylene-polyoxypropylene block copolymer; and (g) water for the balance.

When used, the present oral disinfectant composition for companion animals is generally prepared by diluting about 1 part of the composition by volume with about 2–5 parts water by volume.

Another embodiment of this invention includes a medicament to prevent or treat companion animal periodontal disease wherein about 1 part by volume of the composition is diluted with about 2–5 parts by volume of water or a medicament to prevent or treat companion animal gingivitis wherein about 1 part by volume of the composition is diluted with about 2–5 parts by volume of water. The compositions listed above are generally diluted with water before use because the recited compositions are concentrated for convenient storage and transportation.

The pharmaceutical effects of the oral disinfectant composition of the present invention on companion animals may include (1) disinfecting the oral cavity;

(2) lowering the pH value in the oral cavity and promoting the secretion of saliva with the result that it is effective in eliminating bad breath and relieving inflammations in gingivae, periodontia and mucous membranes in the oral cavity;

(3) relieving oral inflammations;

(4) tightening of gingivae;

(5) preventing periodontitis disorders and retarding reattachment of plaque to the teeth; and (6) preventing bad breath.

BRIEF DESCRIPTION OF THE DRAWINGS

FIG. 2 shows a Stephane curve after applying the oral disinfectant composition of the present invention to the oral cavity of dogs and cats.

DETAILED DESCRIPTION

Figure 1:
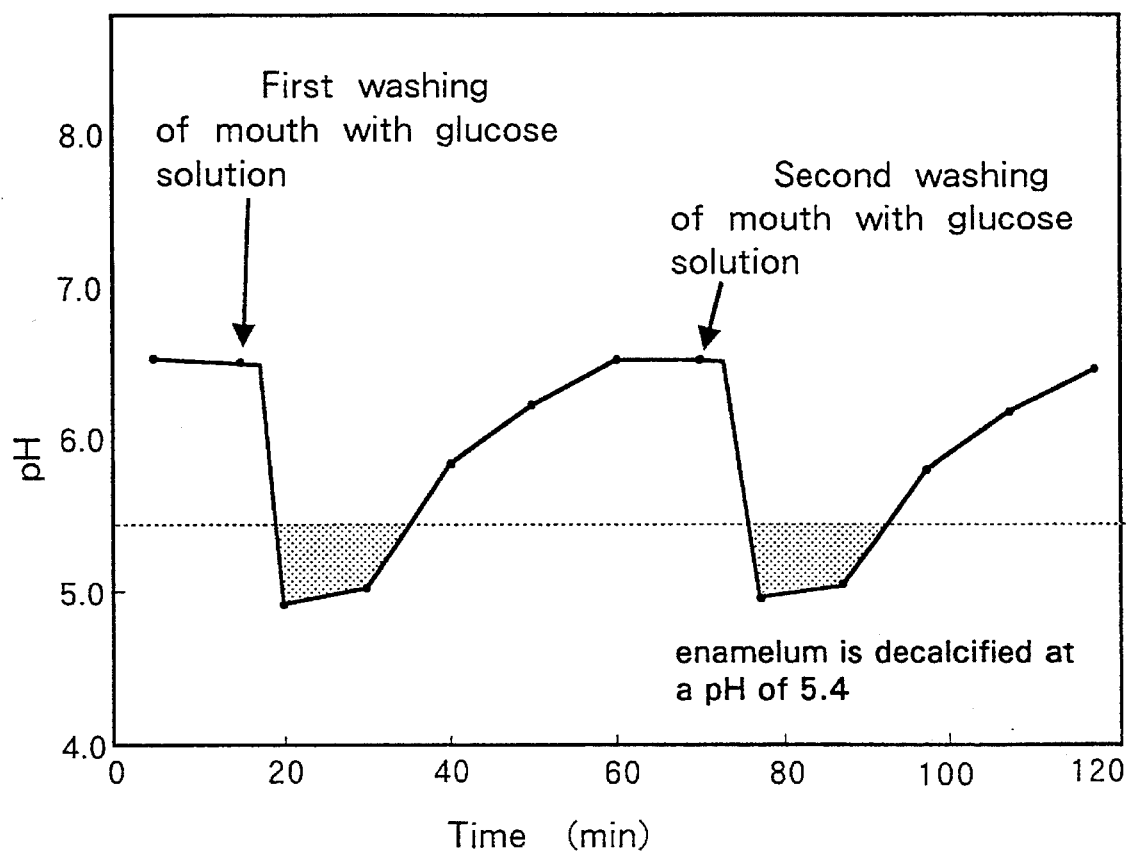
FIG. 1 shows a Stephane curve indicating the general decalcifying activity of acids in the oral cavity.

The oral disinfectant composition of this invention includes a fatty acid monoester, one or more fatty acids, an acid or chelating agent, a polyalcohol, a surfactant and water.

Fatty Acid Monoesters

Fatty acid monoesters are used in the composition because these esters have anti-microbial activity against gram-positive microbes as well as against gram-negative microbes when combined with a synergistic acid or chelating agent. Preferred fatty acid monoesters which may be used in the present composition include known glycerol monoesters of lauric, caprylic and capric acid and/or propylene glycol monoesters of lauric, caprylic or capric acid. The glycerol monoester of lauric acid is particularly preferred. These monoesters have been reported to be food grade and are generally recognized as safe (GRAS) materials. These monoesters are reported to be effective as food preservatives and effective as topical pharmaceutical agents. For example, Kabara, *J. of Food Protection,* 44:633–647 (1981) and Kabara, *J. of Food Safety,* 4:13–25 (1982) report that LAURICIDIN (the glycerol monoester of lauric acid commonly referred to as glycerol monolaurate or monolaurin), a food grade phenolic and a chelating agent may be useful in designing food preservative systems. These reports also indicate that the presence of acid or chelating agents enhances the microbial spectrum and activity of monolaurin. Bell et at., *Meat Ind. Res. Inst.,* 4:4 (1987) report that sorbic acid and monolaurin may be useful luncheon meat preservatives. Ueno et al., U.S. Pat. No. 4,299,852 report that sorbic acid and monolaurin may be used in a process to prepare botulinal-resistant meat products.

The amount of fatty acid monoesters in the present composition is preferably from 0.1 to 3 wt %, more preferably from 0.5 to 1.5 wt % of the total weight of the composition.

Fatty acids

Fatty acids for use in this composition include fatty acids having from 6 to 14 carbon atoms. One or more than one acid selected from among these fatty acids may be employed. These fatty acids are believed to be effective for lowering the pH value in the oral cavity. Preferred acids are caprylic acid and capric acid or a combination thereof. The total amount of fatty acids in the present composition is preferably from 0.5 to 10 wt %. A more preferred amount is from 1.8 to 3.8% of caprylic acid along with from 1 to 3 wt % of capric acid.

Acid or Chelating Agents

In this invention, acid or chelating agents which may be used in the composition are also generally food grade and/or generally recognized as safe, GRAS, materials. Preferred acid or chelating agents include lactic acid, tartaric acid, adipic acid, succinic acid, citric acid, ascorbic acid, malic acid, mandelic acid, acetic acid, sorbic acid, sodium acid pyrophosphate, acidic sodium hexametaphosphate (such as SPORIX acidic sodium hexametaphosphate), and ethylenediaminetetraacetic acid and salts thereof. These materials are typically components which have been used with glycerol fatty acid esters to provide useful topical antimicrobial pharmaceutical compositions and preservative compositions. See, e.g., Kabara, EPO 0 243 145 published Oct. 28, 1987 and Karbara, EPO 0 244 144 published Nov. 4, 1987. The amount used in the present composition is preferably from 2 to 10 wt %.

Polyalcohols

Polyalcohols are incorporated in the composition because they are effective for dissolving the above-mentioned components and are not toxic to animals. Preferred polyalcohols such as polyethylene glycol and propylene glycol will dissolve fatty acid monoesters in water and thus facilitate the use of the resulting solution. The amount to be used in the composition is preferably from 10 to 50 wt %. When propylene glycol is used, the amount is preferably from 15 to 30 wt %.

Surfactants

Surfactants are used to help dissolve the fatty acid monoesters in water. A preferred surfactant is polyoxyethylene-polyoxypropylene block copolymers. The amount used in the composition is preferably from 2 to 30 wt %, and more preferably from 5 to 15 wt %. The surfactants do not retard the anti-microbial activity of the composition of this invention against microorganisms which are present in the oral cavity.

Water for the Balance of Composition

Water to be used can be selected from any water source such as distilled water, sterilized pure water, hard water and soft water, etc.

The essential components constituting the composition of the present invention are listed above. If desired, the composition may contain small amounts of colorants and flavorants.

The composition of the present invention may be prepared by combining the above described components using processes and procedures well known to those of ordinary skill in the art. Briefly, a concentrated composition is prepared by adding PLURONIC F-68 surfactant to cold deionized water and then adding lactic acid to the cold mixture to form a first solution. A second solution is prepared by adding glycerol monolaurate, caprylic and capric acid to propylene glycol. The final composition is then prepared by heating the first solution to about 160° F. and heating the second solution to about 140° F. The heated solutions are then combined and allowed to cool to ambient temperature with constant mixing.

The components and/or reagents listed in the examples are commercially available from the following sources: glycerol monolaurate (Lauricidin Inc., Okemos, Mich.), PLURONIC F-68 (BASF, Parisippany, N.J.), propylene glycol monolaurate, monocaprate, and monocaprylate (Unichema North America, Chicago, Ill.), propylene glycol (J. T. Baker, Inc., Phillipsburg, N.J.), acetic acid, citric acid, mandelic acid (Mallinckrodt, Inc., Paris, Ky.), and lactic acid (R.I.T.A. Corp., Woodstock,Ill).

Since the recited oral disinfectant composition is highly concentrated, it is generally diluted with water (typical dilutions include about 1 part by volume concentrate to about 2–5 parts by volume water) before use. A cotton ball is dipped in the aqueous dilution and the composition is liberally applied to the teeth, the periodontia and the mucous membranes in the oral cavity while massaging them with the cotton ball. Other applicators may be used or the aqueous dilution may be sprayed over teeth and into the oral cavity.

First, when applied to the mouth, the oral disinfectant lowers the pH value in the mouth as its pH value itself is low. Secondly, it promotes secretion of saliva, as it has a low pH value. Accordingly, it may control the formation of plaque via the actions of enzymes such as lysozymes and lactoferrins. Thirdly, due to the antimicrobial activity of the fatty acid monoesters at low pH values, the oral disinfectant of the present invention may exterminate various microorganisms in the oral cavity and control the generation of plaque.

The oral disinfectant of the present invention acts to disinfect the oral cavity, lower its pH value and promote the secretion of saliva. Thus it reduces the number of oral bacteria which helps to eliminate bad breath and relieve inflammations in the gingivae, the periodontia and the mucous membranes in the oral cavity. As it lowers the pH value in the oral cavity, the gingivae of affected animals may be tightened, the animals may be easier to feed, their appetite may be increased and, hence, they may have a fine and glossy coat of hair and become healthy.

When gram-negative oral flora become more active, they generate endotoxins which may cause diarrhea, hepatic disorders, etc. Since the oral disinfectant composition of the present invention is also effective against such gram-negative microbes, it may prevent internal diseases. In addition, it may reduce the re-attachment of plaque to the teeth.

The oral disinfectant of the present invention improves the oral conditions in companion animals because it reduces the number of oral bacteria, lowers the pH value in the oral cavity, disinfects the oral cavity, promotes the secretion of saliva, and reduces the accumulation of plaque (plaque is a cause of periodontal disease on the teeth.

Specifically, various microorganisms may be killed by the oral disinfectant of the present invention. Aerobic microbes known to cause gingivitis (gram-positive microbes, gram-negative microbes, fungi and anaerobic microbes) are killed. Anaerobic microbes known to cause periodontitis, such as Bacteroides, Spirochaeta, etc., are also killed. Thus, the oral disinfectant composition of the present invention may exterminate microorganisms causing gingivitis and periodontitis and, therefore, it is useful for treating and preventing inflammations caused by those diseases.

All the components constituting the oral disinfectant of the present invention are widely used or recognized as food additives and pharmaceutical ingredients in foods and medicines, and these have been accepted for example, in Japan according to the Food Sanitation Act and the Drugs, Cosmetics and Medical Instruments Act. In the United States of America, they have also been widely used or are recognized as GRAS (generally recognized safe).

When the oral disinfectant composition of the present invention is applied to the oral cavity, the decalcifying effect by the acids contained in the composition should be taken into consideration since the pH value of the composition is low. In the field of odontology, a Stephane curve is known as a standard for determining enamel decalcification. See, for example, "Why are carious teeth formed", Iwanami Shin-sho by S. Hamada, p. 88. According to such a Stephane curve, it may be determined whether the enamel of teeth is damaged by acids that reduce the inorganic components in the tooth enamel.

FIG. 1 shows an ordinary Stephane pH curve. From this, it is noted that decalcification occurs when the pH value in the oral cavity becomes less than 5.4. Considering this, the oral disinfectant of the present invention was subjected to the same test. The test result is shown in FIG. 2. In FIG. 2, the oral disinfectant of the present invention was applied to the teeth of dogs and cats, after scaling, and the pH value in their oral cavity was measured. From these measurements, it is noted that the pH value in the animals' oral cavity did not remain in the danger range of 5.4 or lower after the disinfectant had been applied. The pH value in their oral cavity became 6 or more in an extremely short period of time after the application, even though the disinfectant itself had a pH value ranging from 2 to 3.

In addition, continuous use of the oral disinfectant of the present invention, maintained the pH value in the animals' oral cavity at a value less than 8 for a long period of time which retarded the symptoms of halitosis and other periodontitis disorders.

EXAMPLES

The following examples are intended to provide further details and embodiments related to the practice of the present invention. These examples are provided for illustrative purposes and should not be construed to limit the scope of the present invention which is defined in the appended claims.

The following oral disinfectant compositions were prepared to be subjected to pharmaceutical tests.

Composition 1:
(a) Glycerol monoester of lauric acid: 1 wt %
(b) Caprylic acid: 2.8 wt %
(c) Capric acid: 2 wt %
(d) Lactic acid: 6 wt %
(e) Propylene glycol: 20 wt %
(f) Polyoxyethylene-polyoxypropylene glycol block copolymer PLURONIC F-68: 10 wt %
(g) water for the balance Composition 2:
(a) Glycerol monoester of lauric acid: 0.7 wt %
(b) Caprylic acid: 2 wt %
(c) Capric acid: 1 wt %
(d) Citric acid: 5 wt %
(e) Propylene glycol: 24 wt %
(f) Polyoxyethylene-polyoxypropylene glycol block copolymer PLURONIC F-68: 7 wt %
(g) water and a small amount of a fragrant material for the balance For both of the listed compositions, 1 part by volume of the composition was diluted with 3 parts by volume water. The diluted compositions were then applied to the oral cavity of dogs and cats according to the regimen cited in Table 1 and the effect of the compositions was determined on the basis of the conditions of the treated animals. The criteria for determining the pharmaceutical effect of the compositions are listed in Table 2. Precisely, bad breath and tartar, if any, were determined by the criteria listed in Table 2 and the pharmaceutical effects of the tested compositions were evaluated at regular intervals. Table 3 shows the criteria for evaluating stomatitis, if any, in the tested dogs and cats. Table 4 shows the test results of the oral disinfectant compositions of the present invention applied to cats, while Table 5 shows those applied to dogs. From the results, it is noted that the oral conditions of all the tested animals were worse in the first examination but then the hygienic conditions in their oral cavity were extremely improved and their stomatitis was noticeably cured after they were treated with the oral disinfectant compositions for one to two months.

TABLE 1

Application of the Disinfectant

| | Treatment | |
| --- | --- | --- |
| 1 to 15 days | Applied once a day | A cotton ball is dipped in a solution of the disinfectant and applied to the oral tissues including gingivae while massaging. The reattachment of tartar to the teeth is evaluated. |
| 16 to 30 days | Applied every three days | |
| 31 days and further | Applied every three days to every week | |

TABLE 2

Criteria for Determination of Oral Sanitation of Dogs and Cats

| Bad Breath | Points | Tartar (Upper P4, Lower M1) | Points |
| --- | --- | --- | --- |
| No bad breath | 0 | No tartar | 0 |
| While being in contact with the tested animals, could smell their bad breath | 1 | Superior margin tartar spotted and attached to ½ or less of the surfaces of the teeth | 1 |
| When the tested animals come near, could smell their strong bad breath | 2 | Superior margin tartar attached in patches to ½ or less of the surfaces of the teeth | 2 |

TABLE 3

Criteria for Diagnosis of Stomatitis of Dogs and Cats

| Symptoms | Points |
| --- | --- |
| Almost no stomatitis inflammation was found in tested animals | 0 |
| Light bleeding and some stomatitis inflammations were found partly in the mucous membrane in their oral cavity, but the tested animals had no problem in feeding | 1 |
| They could feed, but some ulcers were found in a part of the mucous membranes in their oral cavity | 2 |
| They could feed only with difficulty because of pain, crater-like ulcers were formed broadly in the mucous membranes in their oral cavity | 3 |

TABLE 4

Effect in Cats

| Tested Animals | | | Criteria for Oral Sanitation | | | | Criteria for Stomatitis | | | | |
| --- | --- | --- | --- | --- | --- | --- | --- | --- | --- | --- | --- |
| Type | Sex | Age | At the First Exam | After 1 Mo. | After 2 Mos. | After 3 Mos. | At the First Exam | After 1 Mo. | After 2 Mos. | After 3 Mos. | Evaluation |
| Jpn cat | M | 5 | 4 | 0 | 0 | 0 | 3 | 2 | 1 | 0 | good |
| Jpn cat | M | 0.5 | 2 | 0 | | | 0 | 0 | | | good |
| Persian cat | M | 10 | 4 | 0 | 0 | 0 | 0 | 0 | 0 | 0 | good |
| Jpn cat | F | 4.5 | 4 | 0 | | | 3 | 2 | | | good |
| Jpn cat | M | 7 | 4 | 0 | | | 3 | 2 | | | good |

TABLE 5

| | | | Effect in Dogs | | | | | | | | |
|---|---|---|---|---|---|---|---|---|---|---|---|
| Tested Animals | | | Criteria for Oral Sanitation | | | | Criteria for Stomatitis | | | | |
| Type | Sex | Age | At the First Exam | After 1 Mo. | After 2 Mos. | After 3 Mos. | At the First Exam | After 1 Mo. | After 2 Mos. | After 3 Mos. | Evaluation |
| Yorkshire Terrier | M | 6 | 4 | 0 | 0 | 0 | 0 | 0 | 0 | 0 | good |
| Jpn Midget Shiba | F | 10 | 4 | 0 | 0 | 0 | 0 | 0 | 0 | 0 | good |
| Yorkshire Terrier | F | 11 | 2 | 1 | 1 | 1 | 0 | 0 | 0 | 0 | good |
| Mongrel | F | 13 | 4 | 0 | 0 | 0 | 3 | 0 | 0 | 0 | good |
| Shetland | M | 8 | 3 | 0 | 0 | 0 | 0 | 0 | 0 | 0 | good* |
| Saint Bernard | M | 3 | 2 | 0 | 0 | 0 | 0 | 0 | 0 | 0 | good |
| Saint Barnard | M | 3 | 2 | 0 | 0 | 0 | 0 | 0 | 0 | 0 | good |
| Saint Bernard | M | 6 | 3 | 0 | 0 | 0 | 0 | 0 | 0 | 0 | good |

*Scaled three months before the test

The above-mentioned tests confirm the pharmaceutical effects of the oral disinfectant of the present invention in both dogs and cats. Those of ordinary skill in the art will recognize that the present oral disinfectant composition may be used with other domesticated animals.

We claim:

1. An oral disinfectant for companion animals wherein the animal's teeth and oral cavity tissues are treated with a composition comprising
   (a) 0.1–3 wt % of a fatty acid monoester selected from the group consisting of glycerol and propylene glycol monoesters of a $C_6$–$C_{14}$ fatty acid;
   (b) about 0.5–10 wt % of a $C_6$–$C_{14}$ fatty acid;
   (c) about 2–10 wt % of an acid or chelating agent selected from the group consisting of lactic acid, tartaric acid, adipic acid, succinic acid, citric acid, ascorbic acid, malic acid, mandelic acid, acetic acid, sorbic acid, sodium acid pyrophosphate, acidic sodium hexametaphosphate, ethylenediaminetetraacetic acid and salts thereof, and mixtures thereof;
   (d) about 10–50 wt % of a polyalcohol;
   (e) about 2–30 wt % of a surfactant; and
   (g) water for the balance.

2. An oral disinfectant of claim 1 wherein the fatty acid monoester of (a) is a glycerol monoester of lauric acid.

3. An oral disinfectant for companion animals as recited in claim 1 wherein the fatty acid of (b) comprises at least two $C_6$–$C_{14}$ fatty acids.

4. An oral disinfectant for companion animals as recited in claim 1 wherein the fatty acid of (b) is caprylic or capric acid or a mixture thereof.

5. An oral disinfectant for companion animals as recited in claim 1 wherein the polyalcohol is selected from the group consisting of polyethylene glycol and propylene glycol.

6. An oral disinfectant for companion animals wherein the animal's teeth and oral cavity tissues are treated with a composition comprising
   (a) about 0.1–3 wt % glycerol monoester of lauric acid;
   (b) about 0.5–10 wt % caprylic acid or capric acid or a mixture thereof;
   (c) about 2–10 wt % lactic acid or citric acid or a mixture thereof;
   (d) about 10–50 wt % propylene glycol;
   (e) about 5–15 wt % polyoxyethylene-polyoxypropylene block copolymer; and
   (f) water for the balance.

7. An oral disinfectant for companion animals as recited in claim 6 comprising
   (a) about 0.5–1.5 wt % glycerol monoester of lauric acid;
   (b) about 1.8–3.8 wt % caprylic acid;
   (c) about 1–3 wt. % capric acid;
   (d) about 4–10 wt % lactic acid;
   (e) about 15–30 wt % propylene glycol;
   (f) about 5–15 wt % polyoxyethylene-polyoxypropylene block copolymer; and
   (g) water for the balance.

8. An oral disinfectant for companion animals prepared by diluting about 1 part by volume of a composition of claim 1 with about 2–5 parts by volume of water.

9. A medicament to prevent or treat companion animal periodontal disease wherein about 1 part by volume of a composition of claim 1 is diluted with about 2–5 parts by volume of water.

10. A medicament to prevent or treat companion animal gingivitis wherein about 1 part by volume of a composition of claim 1 is diluted with about 2–5 parts by volume of water.

* * * * *